US008172824B2

(12) United States Patent
Pfeifer et al.

(10) Patent No.: US 8,172,824 B2
(45) Date of Patent: May 8, 2012

(54) APPARATUS FOR COMBINING COMPONENTS UNDER STERILE CONDITIONS

(75) Inventors: Thomas Pfeifer, Eschenbürg (DE); Dietmar Palm, Wohratal (DE); Michael Becker, Dautphetal-Holzhausen (DE); Michael Seipp, Burgwald-Bottendorf (DE); Rainer Wabnegg, Wetter-Amoenau (DE)

(73) Assignee: CSL Behring GmbH (DE)

( * ) Notice: Subject to any disclaimer, the term of this patent is extended or adjusted under 35 U.S.C. 154(b) by 1244 days.

(21) Appl. No.: 10/231,151

(22) Filed: Aug. 30, 2002

(65) Prior Publication Data

US 2003/0069538 A1 Apr. 10, 2003

(30) Foreign Application Priority Data

Aug. 31, 2001 (DE) .................................. 101 42 450

(51) Int. Cl.
*A61B 19/00* (2006.01)

(52) U.S. Cl. ........ 604/414; 604/411; 604/412; 604/415; 604/416

(58) Field of Classification Search .......... 604/410–416, 604/264, 905, 403; 215/277; 206/363
See application file for complete search history.

(56) References Cited

U.S. PATENT DOCUMENTS

| | | | | | |
|---|---|---|---|---|---|
| 4,180,070 | A | * | 12/1979 | Genese | 604/88 |
| 4,898,209 | A | | 2/1990 | Zbed | |
| 5,445,631 | A | * | 8/1995 | Uchida | 604/412 |
| 5,743,312 | A | | 4/1998 | Pfeifer et al. | |
| 5,879,345 | A | * | 3/1999 | Aneas | 604/411 |
| 6,090,092 | A | * | 7/2000 | Fowles et al. | 604/413 |
| 6,090,093 | A | | 7/2000 | Thibault et al. | |
| 6,113,583 | A | * | 9/2000 | Fowles et al. | 604/403 |
| 6,159,192 | A | | 12/2000 | Fowles et al. | |
| 6,537,263 | B1 | * | 3/2003 | Aneas | 604/412 |
| 6,571,837 | B2 | * | 6/2003 | Jansen et al. | 141/329 |
| 6,699,229 | B2 | * | 3/2004 | Zinger et al. | 604/410 |

FOREIGN PATENT DOCUMENTS

| | | | |
|---|---|---|---|
| DE | 0 737 467 | B1 | 10/1996 |
| DE | 196 04 113 | C2 | 10/2000 |
| EP | 0 614 653 | A2 | 9/1994 |
| EP | 0 737 467 | B1 | 10/1996 |

* cited by examiner

*Primary Examiner* — Leslie Deak
(74) *Attorney, Agent, or Firm* — Finnegan, Henderson, Farabow, Garrett & Dunner, LLP

(57) ABSTRACT

An apparatus for combining under sterile conditions a liquid component held in a first container and a solid or liquid component held in a second container is provided. In one embodiment, two hollow bodies for receiving the two containers are provided, the two hollow bodies being arranged one within the other and being slidable relative to one another in a guided manner in the longitudinal direction. A cannula holder forms a pot-shaped structural unit with the first hollow body. Alternatively, the cannula holder is provided with at least one cannula. The cannula holder and the first hollow body may be separate components, in which the cannula holder is pot-shaped.

25 Claims, 7 Drawing Sheets

Figure 1:
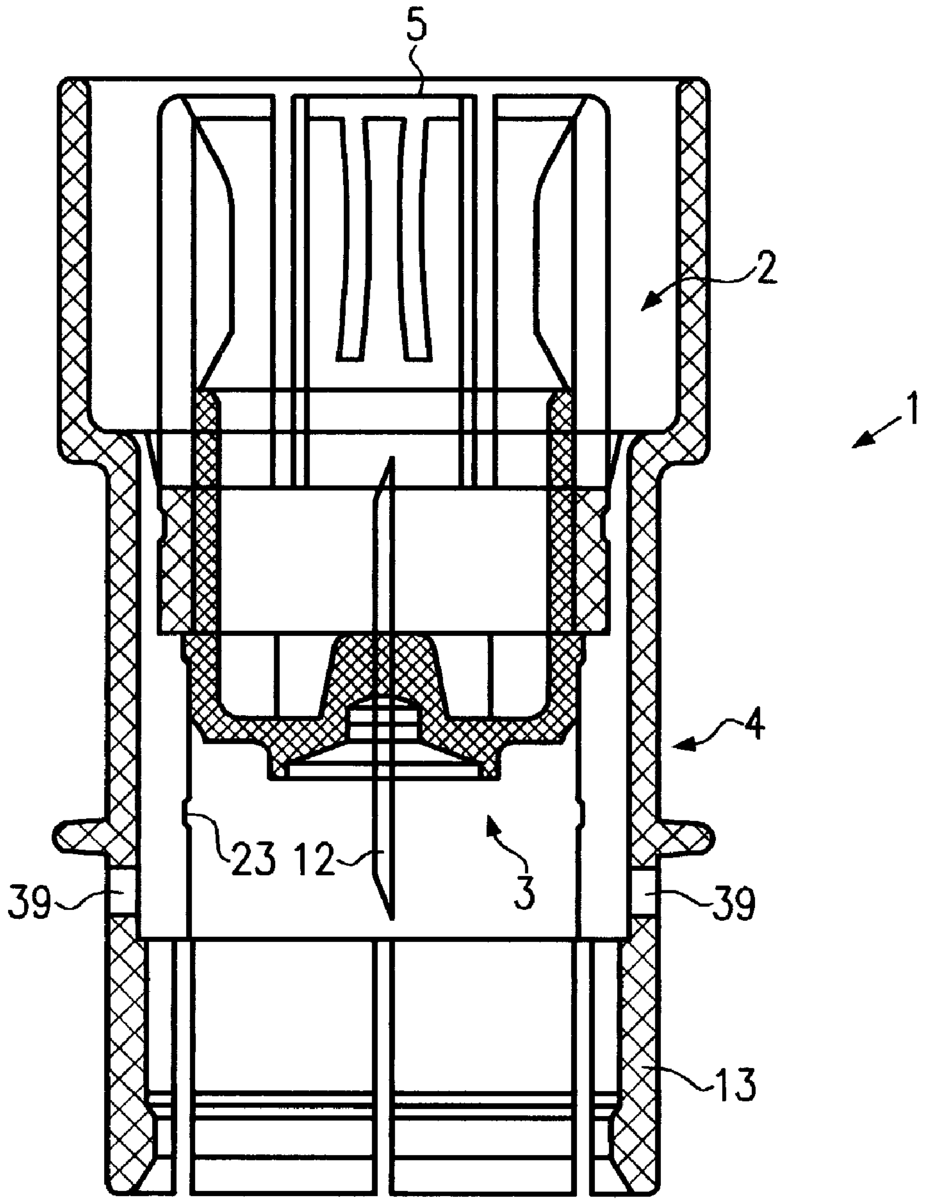

25
27
26
29
2
3
4
28
1
12

APPARATUS FOR COMBINING COMPONENTS UNDER STERILE CONDITIONS

The invention relates to an apparatus for combining under sterile conditions a liquid component held in a first container and a solid or liquid component held in a second container.

Such an apparatus which can be preassembled is known from the prior art. It is an apparatus for transferring a solvent from one flask into a second flask containing a pharmaceutical product in order to dissolve the product. Such a transfer system is classed as a single-use medical item. In order to simplify handling of the reconstitution process, the two glass flasks are preassembled into the transfer apparatus. Sterile packaging ensures that the reconstituted product can be stored for up to 36 hours.

An apparatus of the type mentioned at the outset is described in EP 0 737 467 A1. There, a single hollow body serves to receive the two containers. Using a two-step mechanism a secured directed transfer is achieved by the closure of the first container having the liquid component first being penetrated by a cannula and then a cannula holder receiving the cannula being pushed by this container in the direction toward the second container receiving the solid or liquid component, so that its closure is penetrated by the cannula. The cannula holder receives a single cannula which is sufficient for combining the components, since before the second container is pierced, a vacuum prevails therein. The cannula holder is designed as a lamellar body orientated perpendicularly to the longitudinal direction of the hollow body receiving the two containers and is connected via retainer bridges to the inner wall of the hollow body, the retainer bridges being able to be ruptured by applying a manual force which is greater than the penetration force of the cannula on penetrating the closure stopper of the first opened container.

A disadvantage in this apparatus is that the cannula holder which is first firmly connected to the hollow body is not separated in a defined manner from the hollow body. Depending on the manner of force introduction, possibly unsymmetrical force introduction, retainer bridges first tear in one region of the cannula holder, as a result of which there is the risk that the cannula holder and thus the cannula swing into a tilted position with respect to the longitudinal direction of the two containers. The consequence is that in particular the closure of the second container is not exactly penetrated and problems arise on transferring the liquid, in particular from the aspect of the vacuum present.

It is an object of the present invention to develop an apparatus of the type mentioned at the outset in such a manner that exact transfer of the component situated in the first container into the second container is ensured.

The invention proposes two fundamental forms of the apparatus. In both apparatuses, a first cylindrical hollow body is provided for receiving the first container in the region of its closure in a receiver orifice of this hollow body and a second cylindrical hollow body is provided for receiving the second container in the region of its closure in a diametrically disposed receiver orifice.

In any event, in the case of the apparatus according to the first form, the two hollow bodies are inserted one in the other and conducted relative to one another in their longitudinal direction so as to be able to slide, and in addition a cannula holder forming a pot-shaped structural unit together with the first hollow body is provided with at least one cannula held by this. The first hollow body and the cannula holder are thus inseparable, they are a permanent structural unit. The pot-shaped form of the structural unit ensures that the structural unit, in particular in the region of its first hollow body, is conducted in a precise manner in the second hollow body. Preferably, the cannula holder forms the bottom of the pot and the first hollow body forms the pot wall, with the first hollow body not being extended beyond the cannula holder. In order to ensure highly exact guidance, the pot wall should have at least one guide section which interacts with at least one guide section of the second hollow body. The precise guidance of the structural unit owing to its pot-shaped form in the second body ensures that the structural unit and thus the cannula holder does not tilt. During a sliding motion of the cannula holder, the cannula is moved in a defined manner in the longitudinal direction to both hollow bodies via the sliding by means of the first container in the direction toward the second container and penetrates its closure.

Generally, the cannula holder holds the cannula firmly, so that the cannula cannot be slid in its longitudinal direction. Preferably, the cannula holder also holds only one cannula, with vacuum prevailing in the second container. After moving the first container in the direction toward the second container and penetration of the closure of the first container by means of the cannula and further sliding forward of the first container and penetration of closure, the liquid component situated in the first container, on account of the vacuum, passes into the second container and mixes under sterile conditions with the solid or liquid component situated there.

In the context of the inventive teaching according to the two forms, the terms “cannula holder” and “cannula” are to be understood broadly. The cannula holder and the cannula can form two separate components, with the cannula holder consisting in particular of plastic and the cannula in particular of metal. However, it is perfectly conceivable to form the cannula holder and the cannula in one piece, with the cannula being formed in the manner of a mandrel or spike. Preferably, this structural unit consists of plastic. The mandrel/spike, in accordance with the circumstances, has one or two passages. If there is a vacuum in the second bottle, one passage is sufficient.

In the case of the apparatus according to the second form, in contrast to the first form, the two hollow bodies are inserted one within the other and the first hollow body and a pot-shaped cannula holder having at least one cannula held by this form separate components, the first hollow body and the cannula holder being inserted one within the other and being able to slide relative to one another guided in the longitudinal direction of the two hollow bodies. In this variant the first hollow body and the cannula holder are not a structural unit. Instead, the cannula holder, in order to ensure precise guidance during its sliding is constructed in the shape of a pot. The first hollow body serves to hold the first container, while the cannula holder serves for mounting the cannula and its precise guidance in the longitudinal direction of the two hollow bodies. The function of mounting the first hollow body and mounting the cannula is thus, in this form, shifted to two fundamental components, in contrast to the first solution. Obviously, in both forms, the cannula holder can at all events serve for holding more than one cannula, depending on the application.

Whereas, in the first form, the first hollow cylinder is closed in the region of the cannula holder, it is open on both ends in the second form. In this form, the pot wall should have at least one guide section which interacts with at least one guide section of the first hollow body. Expediently, the first hollow body in the first container inserted therein is mounted in the second hollow body so as not to be slidable. If the first container is inserted into the first hollow body, when the first container is advanced, only the pot-shaped cannula holder is pushed forward.

Expediently, the first hollow body forming a structural unit with the cannula holder, or the pot-shaped cannula holder, has latching means for latching, in differing positions of the cannula holder, in complementary latching means of the second hollow body. These latching means ensure defined sliding of the cannula holder and thus of the cannula. If the closure of the first container is to be penetrated before the cannula holder is advanced and before it comes into contact with the closure of the second container, the latching of the cannula holder in this position must be dimensioned so that it does not slide on contact of the closure of the first container with the cannula. Not until the cannula has penetrated this closure does the first container or its closure come against the cannula holder or a component connected to this, so that on advancing the first container the cannula holder is advanced by the externally applied force. In principle, it would also be conceivable to select the penetration strength of the second container closure to be greater than that of the first container closure, so that the second container closure applies resistance with respect to the cannula which, on advancing the first container, leads to its closure being penetrated. In this case, the abovementioned latching would not be necessary.

The second latching serves for fixing the cannula holder or a component connected thereto in the maximally advanced position. It ensures that when the second container is taken out of the second hollow body the cannula holder is not pulled back and consequently the cannula is withdrawn from the second container closure.

Essential aspects of the inventive apparatus are thus the safety in handling and robustness in use due to a novel construction of the cannula holder which is no longer fixed to a cylindrical hollow body and is no longer constructed as a disc. The "pot" form makes possible a much more firmly guided motion during the activation according to the "piston in cylinder" principle. When a single cannula and vacuum conditions in the second container are used, the apparatus is activated in a vertically orientated position by pressure on the first container situated at the top.

Preferably, the first and/or second hollow body is segmentally shaped in the region of its container-side end. This makes it possible to fix the respective container precisely in the assigned hollow body, but makes it possible to move the container relative to the hollow body, with the segments being expanded outward. The segments form, in particular, expanded flaps which surround a crimp-on cap of the respective container. The apparatus is used in particular together with containers which are constructed as vials. These are preferably glass vials having a capacity of 1 to 10 ml.

Preferably, the apparatus has a visual end-point indication, with which, via an inspection window, reaching the end position of the cannula holder and thus penetration of the second container closure by the cannula can be followed. The second hollow body is provided with inspection window or inspection windows on the side for this.

For immediate use, the apparatus, that is to say together with the two containers preassembled in the hollow bodies, is sealed into a pack, in particular a soft blister pack. There is thus no risk of microbiological contamination during the reconstitution procedure, since the transfer process can take place within the sterile outer pack and, in addition, it permits the reconstituted product to be stored under sterile conditions. The inventive apparatus, moreover, prevents the handling of cannulas with freely accessible cannula tips. There is no risk of wounding during removal of the product bottle after reconstitution, because the cannula holder is retained in the apparatus. The apparatus, because of the preassembly of the relevant components, is immediately available. Within a short time the transfer of the liquid can be begun from the first to the second container. This results in a considerable saving in time during the preparation process. The reconstitution can be performed by a single person, either in advance, or directly in the sterile area of an operating theater.

Other features of the invention are described in the patent claims, the description of the figures and in the figures themselves.

Figure 2:
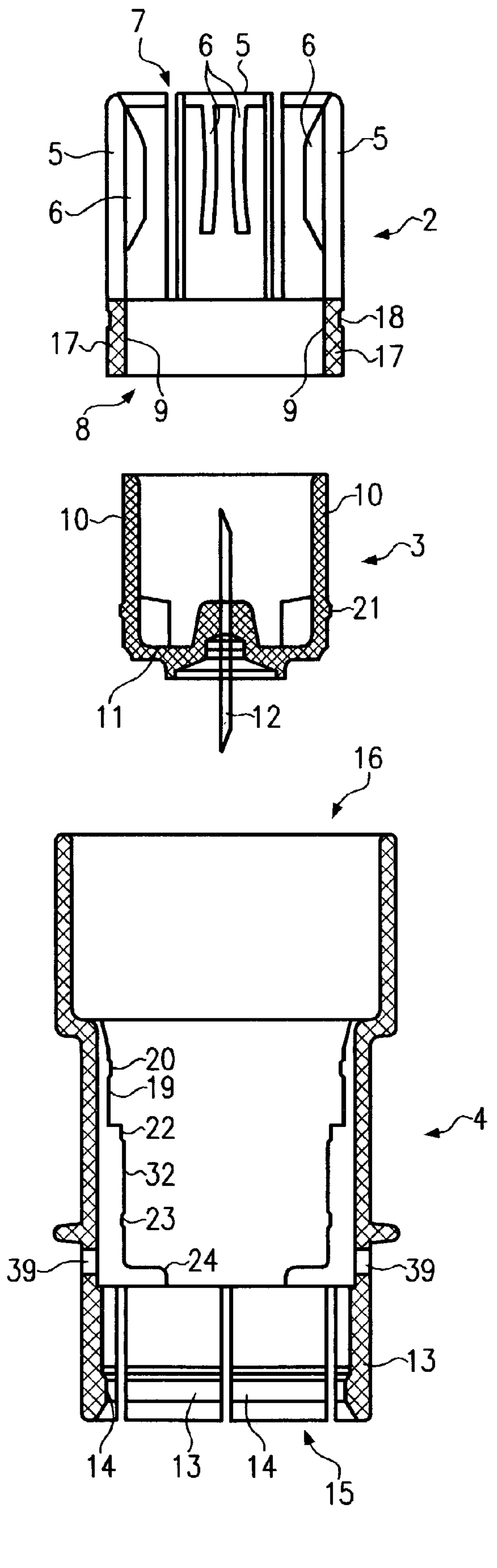
Figures 3A, 3B, 3C, 3D, 3E, 3F:
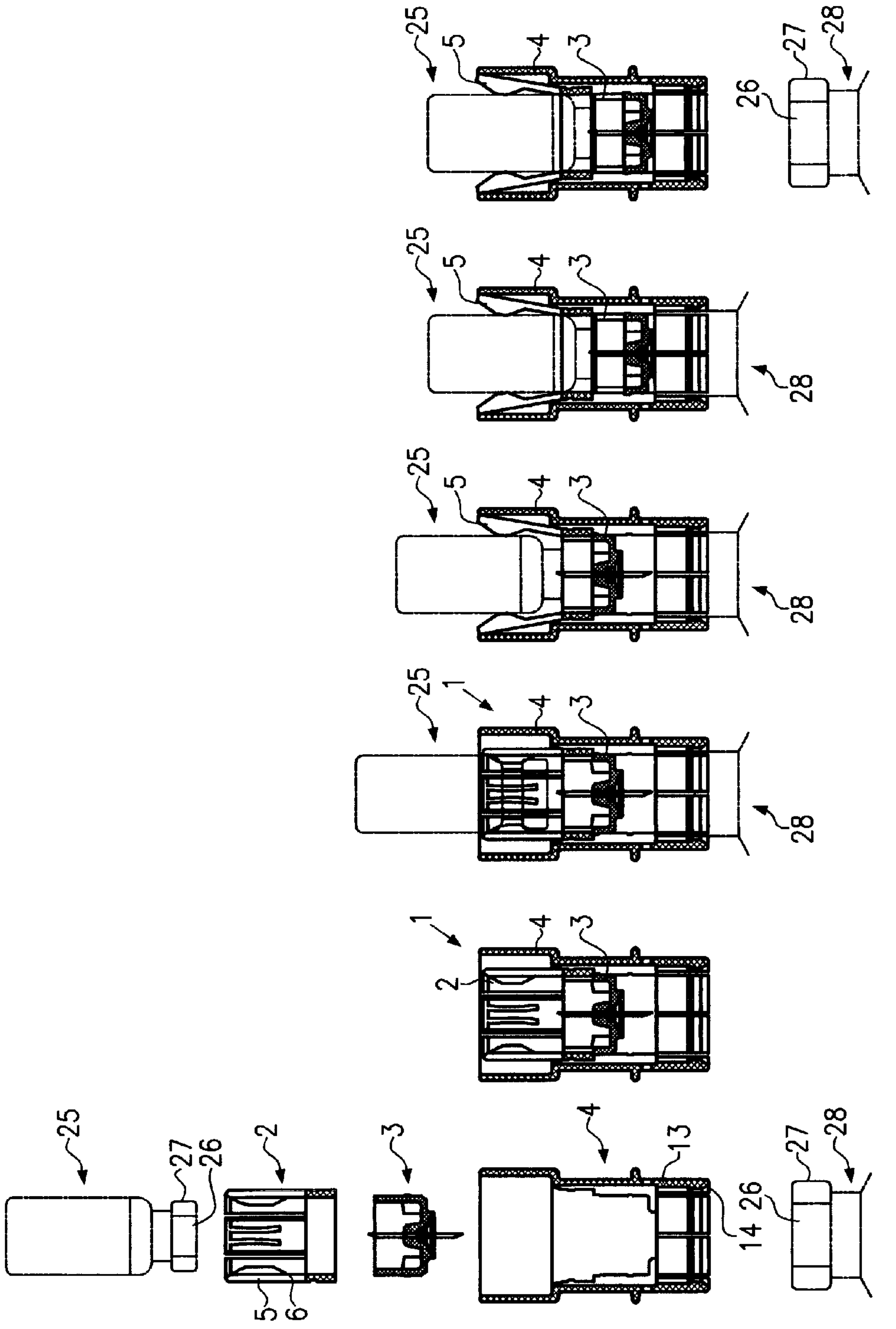
Figure 4:
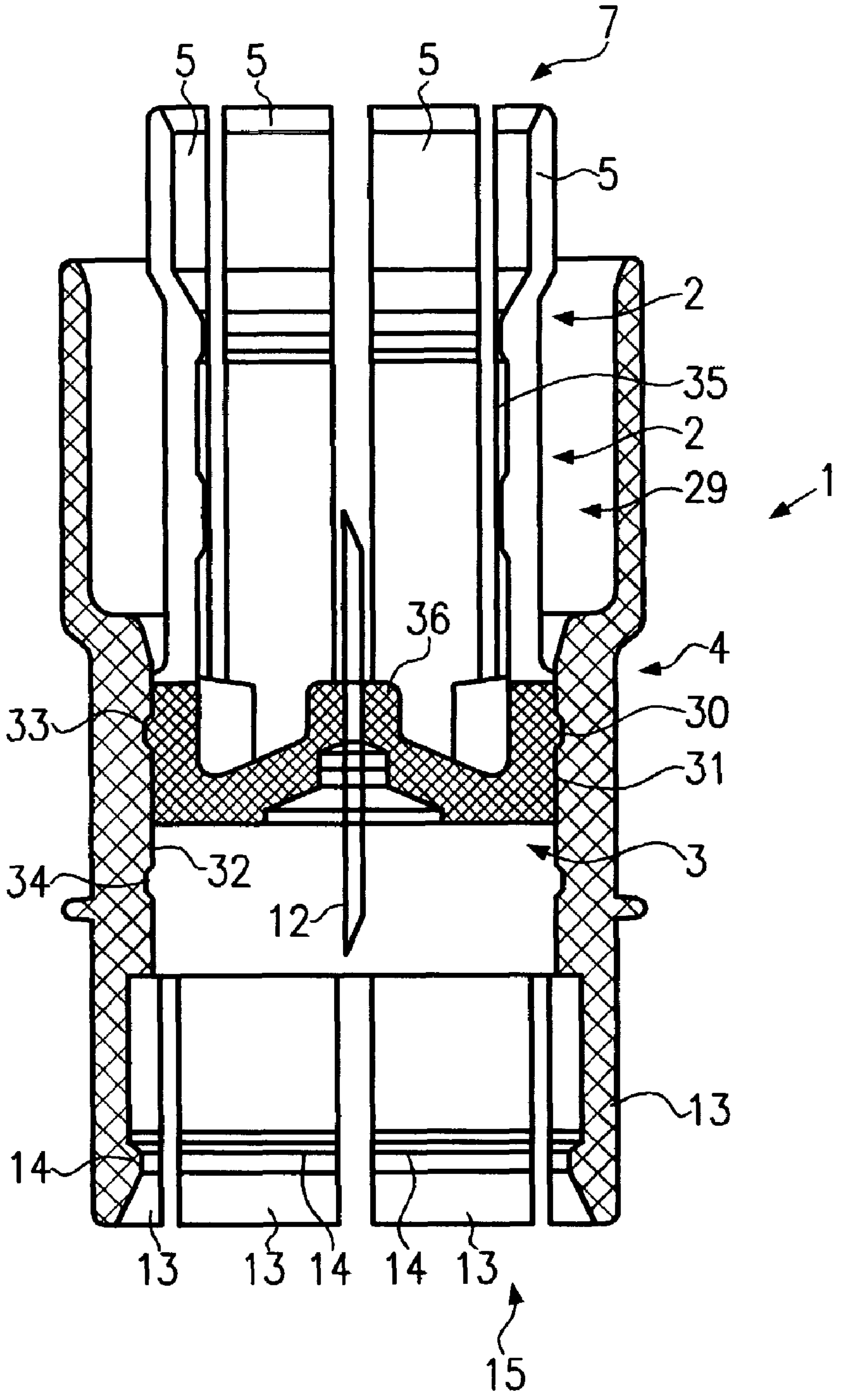
Figure 5:
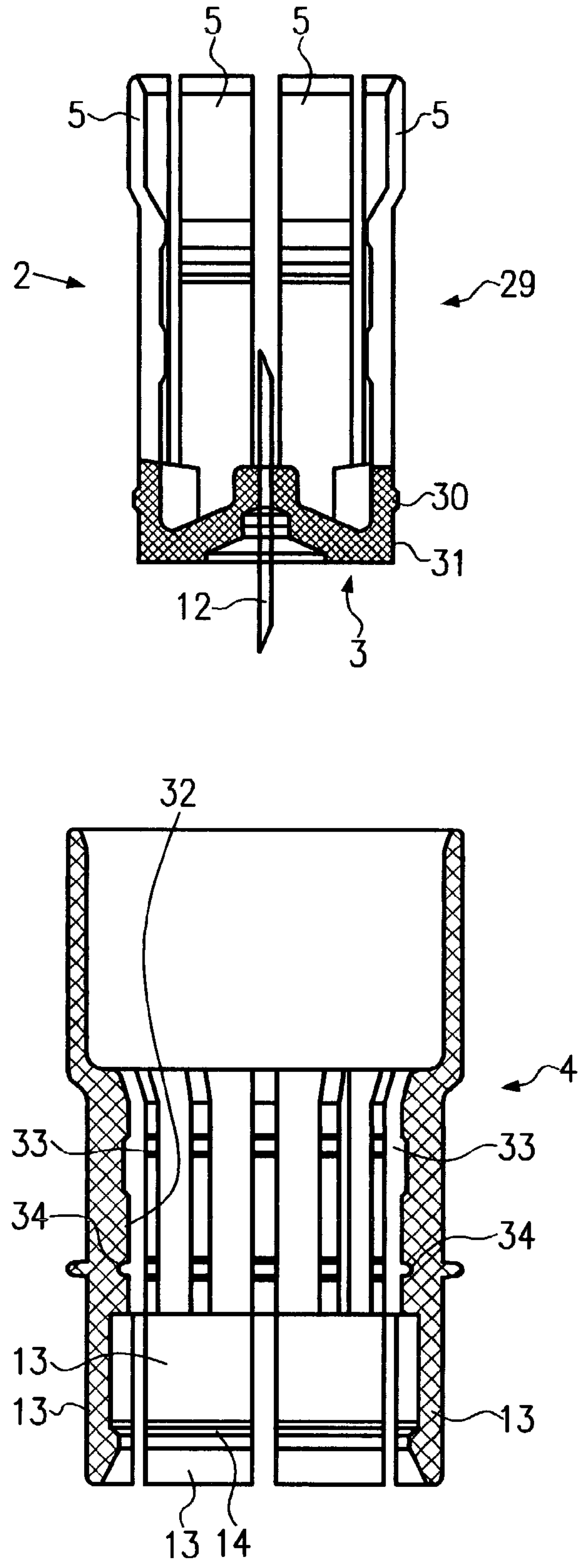

In the figures the invention is illustrated with reference to a number of exemplary embodiments, without being limited to these. In the drawings:

FIG. 1 shows a first embodiment (at the outset called the first form) of the inventive apparatus in preassembled state, shown in cross section, FIG. 2 shows in an exploded view the individual parts of the apparatus shown in FIG. 1, FIGS. 3*a*-3*f* illustrate the assembly and activation steps of the apparatus shown in FIGS. 1 and 2, FIG. 4 shows a second embodiment (at the outset called the second form) of the inventive apparatus in preassembled state, shown in cross section, FIG. 5 shows in an exploded view the individual parts of the apparatus shown in FIG. 4, FIGS. 6*a*-6*f* illustrate the assembly and activation steps of the apparatus shown in FIGS. 4 and 5, and FIGS. 7A to D show drawings of the inventive apparatus sealed in a blister film.

FIGS. 1 and 2 illustrate the inventive apparatus, also called transfer system 1, in a three-piece embodiment.

A first hollow body 2 serves for receiving, so that it is slidable, a pot-shaped cannula holder 3 and can be inserted into the second hollow body 4. The hollow body 2 serves as holder for a solvent bottle and for this purpose it is provided with diverse flexible segments 5 disposed in parallel to the longitudinal axis of the cylindrical hollow body 2. These segments bear inwardly directed beads 6. The orifice 7 of the hollow body 2 which is at the top when the transfer system is being used serves to receive the solvent bottle. In the region of the lower orifice 8, the hollow body 2 is provided with an inner guide section 9 for the cannula holder 3 which is received by this orifice, which cannula holder 3 has an external complementary guide surface 10, so that the cannula holder 3 is guided with little play in the hollow body 2.

The pot-shaped cannula holder 3, in the region of its bottom section 11, firmly holds a central axially-directed transfer cannula 12 which is provided with pointed ends. The length of the transfer cannula 12 is such that each of the projections thereof, based on the bottom section 1 [sic] of the cannula holder 3, are sufficient to penetrate the closures of the containers interacting with the apparatus.

The second hollow body 4 serves for receiving the first hollow body 2 and the cannula holder 3 in its advanced position. The lower end, based on the position of the apparatus in use, of the hollow body 4 is provided with flexible segments 13 corresponding to the form of the hollow body 2 which segments themselves have inward-directed beads 14. The second container which holds the solid or liquid components is inserted into the hollow body 4 through the orifice 15 of the hollow body 4 assigned to these segments 13. In the region of the other orifice 16, the hollow body 4 is widened, so that when hollow body 2 is inserted in this, its flexible segments have sufficient space to be expanded outward. The hollow body 2 is held in the hollow body 4 in the region of its lower outer guide section 17 which is provided with a circumferential latching groove 18 into which, in the region of the complementary inner guide section 19, a circumferential latching projection 20 there engages. In the inserted position of the hollow body 2, this is thus fixed with respect to the hollow body 4.

The cannula holder 3 also has a circumferential latching projection 21 in the region of its outer guide section 10, which latching projection 21, in the position which is substantially remote from the bottom orifice 11, interacts with an expansion 22 in the hollow body 4. If the cannula holder 3 is subjected to a force directed toward the orifice 15, the cannula holder 3 is advanced until its latching projection 21 latches with a latching groove 23 the hollow body 4 situated further forward in the hollow body 4. In this position the cannula holder 3 lies with its bottom section 11 against a circumferential annular projection 24 of the hollow body 4.

In the completely advanced position of the cannula holder 3, its position can be seen via inspection windows 39 which are formed as holes in the hollow body 4.

FIG. 1 illustrates the assembled state of the transfer system 1 with hollow body 2 inserted into the hollow body 4 before the cannula holder 3 is advanced in the direction of the orifice 15 in the hollow body 4.

All parts of the transfer system 1 described thus far consist of plastic, except for the metal cannula 12.

FIGS. 3A-3F shows the various steps during assembly and activation of the transfer system 1. In FIG. 3A, the individual component diagram of FIG. 2 is illustrated. In addition, the glass bottle 25 provided for insertion into the hollow body 2 and which receives the solvent. The bottle 25 is provided with an elastic penetrable closure 26 and has a crimp-on cap 27 in the region of the closure. The other glass bottle 28, which can be inserted into the hollow body 4 from below, and holds the solid or liquid component, is formed correspondingly. In the orientation shown in FIG. 3*a* with glass bottle 25 at the top and glass bottle 28 at the bottom, the glass bottle 25 is inserted into the hollow body 2 and the glass bottle 28 into the hollow body 4. In the course of this, as shown in FIG. 3*c*, the beads 6 of the segments 5 and the beads 14 of the segments 13 engage with the bottles 25 and 28, respectively, with the bottle 28 lying on the annular projection 24 of the hollow body 4. If the two bottles 25 and 28 are then pressed toward one another, or the glass bottle 25 is pressed further into the hollow body 2, the cannula 12 of the cannula holder 3, while remaining in its centralized position, penetrates the closure 26 of the bottle 25. When the bottle is advanced over the bottle body [sic] having a greater diameter, the segments 5 of the hollow body 1 are expanded outward, as shown in FIGS. 3*d*. If further force is exerted on the two bottles 25 and 28, or if bottle 25 is again moved into the hollow body 2, this leads, owing to the bottle 25 lying against the cannula holder 3, to its sliding toward the orifice 15 of the hollow body 4. In the course of this the other end of the cannula 12 penetrates the closures 26 of bottle 28. When this stage is reached, as shown in FIG. 3*e* the latching projection 21 of the cannula holder 3 engages with the latching groove 23 in the hollow body 4. After transfer of the liquid into the bottle 28, this is removed from the transfer system as illustrated in FIG. 3*f*.

The embodiment according to FIGS. 4 and 5 differs from that according to FIGS. 1 and 2 in that, instead of the two components—hollow body 2 and cannula holder 3—one component 29 is provided which itself combines the function of these two components. Components which match the embodiment according to FIGS. 1 and 2 and the functional illustration according to FIG. 3 are, for the sake of simplicity, marked with the same reference numbers in FIGS. 4 and 5 and the functional illustration according to FIG. 6.

As can be seen in the depiction of FIGS. 4 and 5, the structural unit 29 is formed in the shape of a pot and is formed by the cylindrical hollow body 2 and the cannula holder 3. The structural unit 29 is provided with an outer circumferential latching projection 30 whose function corresponds to that of the latching projection 21 on the cannula holder 3 in the embodiment according to FIGS. 1 and 2. The outer guide section 31 of the structural unit 29 interacts with the inner guide section 32 of the hollow body 4 which, in the two functional positions of the cannula holder 3 of the structural unit 29, is provided with inner latching grooves 33 and 34 which correspond in their function to the expansion 22 or the latching groove 23 of the hollow body 2 in the embodiment described above.

Figures 6A, 6B, 6C, 6D, 6E, 6F:
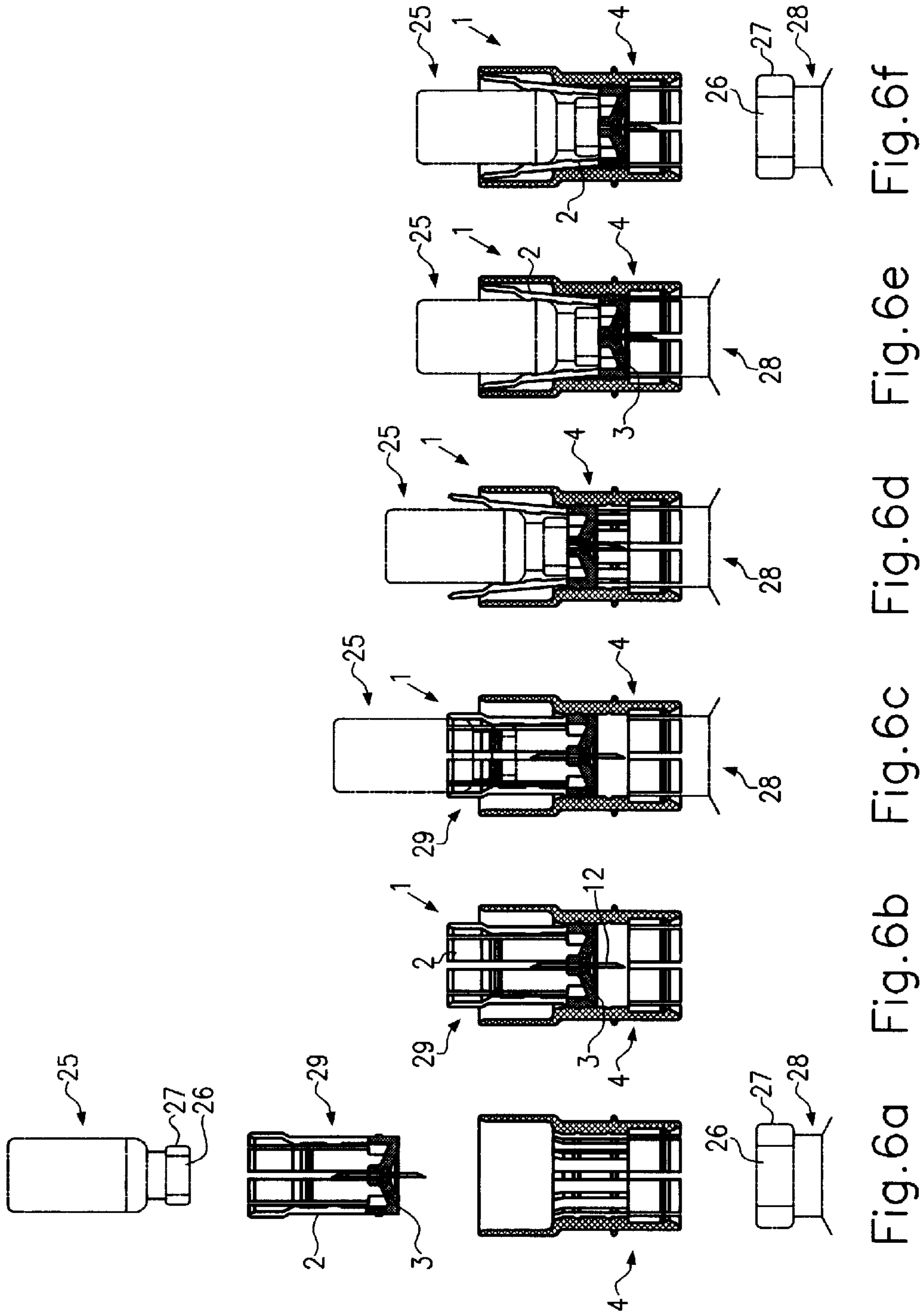

As shown in FIGS. 4 and 6*a*-6*f*, after the transfer system 1 is assembled, the bottles 25 and 28 are inserted, the upper bottle 25 with its crimp-on cap 27 engaging in a circumferential recess 35 of the flexible segments 5 of the structural unit 29. When the bottle 25 is further advanced, as in FIGS. 6*c* and 6*d*, the segments 5 are expanded outward via the bottle body. The crimp-on cap 27 of the bottle 25 is moved against the cannula holder 3, in particular in the region of the projection 36 which holds the cannula 12. When the bottle 25 is advanced further, the structural unit 29 together with its latching projection 30 is moved out of the latching groove 33 of the hollow body 4. The lower end position of the cannula holder 3 is shown in FIG. 6*e*; in this position the latching projection 30 of the structural unit 29 reaches the latching groove 34 of the hollow body 4 and the cannula 12 has pierced the closure 26 of the lower bottle 28. The bottle is then removed as shown in FIG. 6*f*.

FIGS. 7A to 7D illustrate a transfer system 1 together with the bottles 25 and 28 which are inserted into the system, sealed into a blister film, in a state as illustrated in FIGS. 3*e* and 6*c*. The blister film 37 is sealed with a seal paper 38, which is preferably permeable to a sterilizing agent.

Figure 7D:
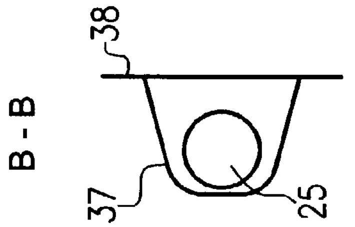
Figure 7C:
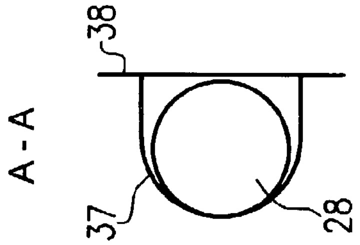
Figure 7A:
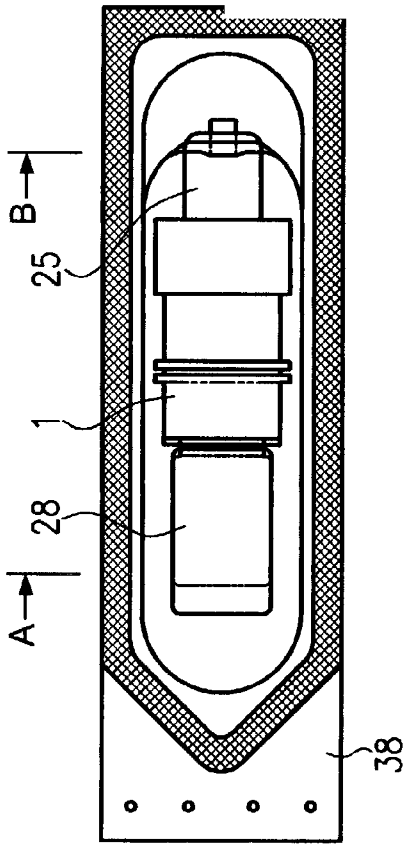
Figure 7B:
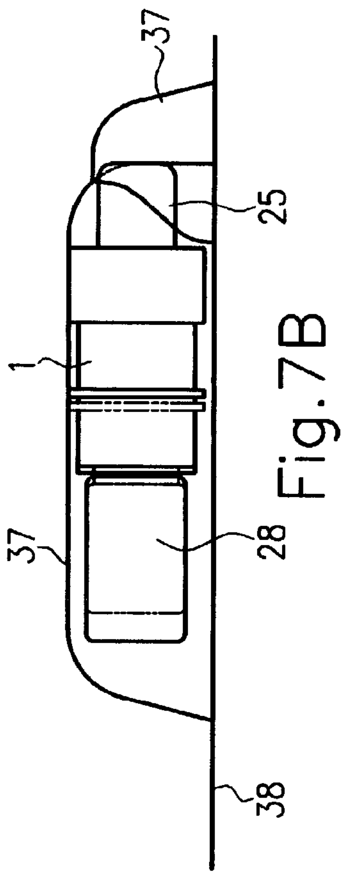

FIG. 7A shows the arrangement in a plan view, FIG. 7B shows this in a side view, and FIGS. 7C and 7D are sections through lines A—A and B—B in FIG. 7A.

| List of reference numbers | |
|---|---|
| 1 | Tansfer system |
| 2 | First hollow body |
| 3 | Cannula holder |
| 4 | Second hollow body |
| 5 | Flexible segments |
| 6 | Bead |
| 7 | Orifice |
| 8 | Orifice |
| 9 | Guide section |
| 10 | Guide section |
| 11 | Bottom section |
| 12 | Transfer cannula |
| 13 | Segment |
| 14 | Bead |
| 15 | Orifice |
| 16 | Orifice |
| 17 | Guide section |
| 18 | Latching groove |
| 19 | Guide section |
| 20 | Latching projection |
| 21 | Latching projection |
| 22 | Widening |
| 23 | Latching groove |
| 24 | Annular projection |
| 25 | Glass bottle |
| 26 | Closure |
| 27 | Crimp-on cap |
| 28 | Glass bottle |

-continued

| List of reference numbers | |
|---|---|
| 29 | Structural unit |
| 30 | Latching projection |
| 31 | Guide section |
| 32 | Guide section |
| 33 | Latching groove |
| 34 | Latching groove |
| 35 | Recess |
| 36 | Projection |
| 37 | Blister film |
| 38 | Sealing paper |
| 39 | Inspection window |

The invention claimed is:

1. An apparatus for combining a first component contained in a first container and a second component contained in a second container, comprising:

a first cylindrical hollow body having a longitudinal axis and including a receiver orifice for receiving a closed end of the first container;

a second cylindrical hollow body having a longitudinal axis and including a receiver orifice for receiving a closed end of the second container;

wherein at least a portion of the first body is configured to be disposed inside the second body; and a cannula holder including at least one cannula;

wherein the cannula holder is a pot-shaped structure, wherein the cannula holder is movable relative to the first cylindrical hollow body, and wherein the cannula holder is configured to be disposed in between the receiver orifice of the first cylindrical hollow body and the receiver orifice of the second cylindrical hollow body during use.

2. The apparatus of claim 1, wherein a wall portion of the cannula holder includes at least one guide section for interacting with at least one guide section of the first cylindrical hollow body.

3. The apparatus of claim 1, wherein the first hollow cylinder body includes two open ends.

4. The apparatus of claim 1, wherein the bottom portion of the cannula holder is disposed below a bottom section of the first cylindrical hollow body.

5. The apparatus of claim 1, wherein a bottom portion of the cannula holder is disposed outside of the first cylindrical hollow body.

6. The apparatus of claim 1, wherein an external surface of the first cylindrical hollow body includes a latching groove and an internal surface of the second cylindrical hollow body includes a latching projection for engaging the latching groove and substantially preventing relative movement between the first and second bodies.

7. The apparatus of claim 1, further comprising means for substantially preventing movement of the cannula holder with respect to the second cylindrical hollow body.

8. The apparatus of claim 7, wherein the means includes a latching projection on an external surface of the cannula holder and a latching groove on an internal surface of the second cylindrical hollow body.

9. The apparatus of claim 1, wherein the first body remains disposed entirely within the second body throughout use of the apparatus.

10. The apparatus of claim 1, wherein the cannula holder includes an open end facing toward the first cylindrical body, and the first cylindrical hollow body is disposed within the second cylindrical body.

11. An apparatus for combining a first component contained in a first container and a second component contained in a second container, comprising:

a first cylindrical hollow body including a first orifice configured to receive a closed end of the first container and a second orifice opposite the first orifice having a inner guide section;

a pot-shaped cannula holder configured to receive the closed end of the first container and having an outer guide section configured to interact with the inner guide section of the first cylindrical hollow body; and a second cylindrical hollow body including a receiver orifice configured to receive a closed end of the second container, wherein the second cylindrical hollow body is configured to receive at least a portion of the first cylindrical hollow body and the cannula holder.

12. The apparatus of claim 11, wherein an external surface of the first hollow body includes a latching groove and an internal surface of the second hollow body includes a latching projection for engaging the latching groove and substantially preventing relative movement between the first and second bodies.

13. The apparatus of claim 11, wherein the first cylindrical hollow body includes a plurality of flexible segments for holding the first container.

14. The apparatus of claim 13, wherein at least one of the flexible segments includes a bead configured to hold the first container in a first position.

15. The apparatus of claim 14, wherein the flexible segments are configured to expand outwardly when the first container is moved to a second position in which the first container is punctured by the cannula.

16. The apparatus of claim 11, wherein the second cylindrical hollow body includes a plurality of flexible segments for holding the second container.

17. The apparatus of claim 11, wherein the second cylindrical hollow body includes at least one window for observing a position of the cannula holder.

18. The apparatus of claim 11, further comprising means for substantially preventing movement of the cannula holder with respect to the second cylindrical hollow body.

19. The apparatus of claim 18, wherein the means includes a latching projection on an external surface of the cannula holder and a latching groove on an internal surface of the second cylindrical hollow body.

20. The apparatus of claim 11, wherein the bottom portion of the pot-shaped cannula holder is disposed below a bottom section of the first cylindrical hollow body.

21. The apparatus of claim 11, wherein a bottom portion of the pot-shaped cannula holder is disposed outside of the first cylindrical hollow body.

22. The apparatus of claim 11, wherein the first body remains disposed entirely within the second body throughout use of the apparatus.

23. The apparatus of claim 11, wherein the cannula holder includes an open end facing toward the first cylindrical body, and the first cylindrical hollow body is disposed within the second cylindrical body.

24. An apparatus for combining a first component contained in a first container and a second component contained in a second container, comprising:

a pot-shaped body having a wall formed by a first cylindrical hollow body and a bottom wall formed by cannula holder, wherein the first cylindrical hollow body includes flexible segments extending in a direction parallel to the longitudinal axis of the first cylindrical hollow body and configured to expand outwardly as a closed end of the first container is advanced within the first cylindrical hollow body toward the pot-shaped body; and a second cylindrical hollow body including a receiver orifice configured to receive a closed end of the second container;

wherein at least a portion of the first cylindrical hollow body is configured to slide within the second cylindrical hollow body.

25. The apparatus of claim 24, wherein the first cylindrical hollow body includes at least one guide section for interacting with at least one guide section of the second cylindrical hollow body.

* * * * *